US005871947A

United States Patent [19]
Paglia et al.

[11] Patent Number: 5,871,947
[45] Date of Patent: Feb. 16, 1999

[54] METHOD FOR THE DETERMINATION OF LOW CONCENTRATIONS OF HEAVY METALS

[76] Inventors: Donald E. Paglia, 15063 Del Gado Dr., Sherman Oaks, Calif. 91403; Stephen W. Renner, 11668 Kiowa Ave., Los Angeles, Calif. 90049; Kanta Bhambhani, 4872 Burnley, Bloomfield Hills, Mich. 48304; Misae Nakatani, 1271 Grand Vista Pl., Monterey Park, Calif. 91754

[21] Appl. No.: 852,564

[22] Filed: May 7, 1997

Related U.S. Application Data

[60] Provisional application No. 60/016,596 May 8, 1996.

[51] Int. Cl.⁶ .............................. C12Q 1/42; C12Q 1/34; C12Q 1/00
[52] U.S. Cl. ................................... 435/21; 435/18; 435/4; 536/26.1; 536/28.53; 536/26.8; 536/28.5; 536/27.8; 536/26.74; 536/27.81; 536/26.72; 556/81; 436/76; 436/800
[58] Field of Search .................................. 435/21, 18, 4; 536/26.1, 28.53, 26.8, 28.5, 27.8, 26.74, 27.81, 26.72; 556/81; 436/76, 800

[56] References Cited

PUBLICATIONS

Cook et al; "Drug and Chemical Toxicology"; (1988 Jun.) vol. 11(2), pp. 195–213 (Abstract).

Public Health Service. Preventing lead poisoning in young children: A statement by the Centers for Disease Control. Atlanta: CDC, 1984.

Bellinger D, Leviton A, Waternaux C, Needleman H, Rabinowitz M. Longitudinal analyses of prenatal and postnatal lead exposure and early cognitive development. *N Engl J Med* 1987; 316:1037–43.

Agency for Toxic Substances and Disease Registry. The nature and extent of lead poisoning in children in the United States: A report to Congress. *Atlanta:ATSDR*, 1988.

Valentine WN, Fink K, Paglia DE, Harris SR, Adains WS. Hereditary hemolytic anemia with human erythrocyte pyrimidine 5'-nucleotidase deficiency. *J Clin Invest* 1974; 54:866–79.

Paglia DE, Valentine WN. Characteristics of a pyrimidine-specific 5'-nucleotidase in human erythrocytes. *J Biol Chem* 1975; 250: 7973–79.

Paglia DE, Valentine WN, Keitt AS, Brockway RA, Nakatani M. Pyrimidine nucleotidase deficiency with active dephosphorylation of dTMP: Evidence for existence of thymidine nucleotidase in human erythrocytes. *Blood* 1983;62:1147–49.

Paglia DE, Valentine WN, Brockway RA. Identification of thymidine nucleotidase and deoxyribonucleotidase activities among normal isozymes of 5'–nucleotidase in human erythrocytes. *Proc Natl Acad Sci* (USA) 1984; 81:588–92.

Paglia DE, Valentine WN, Brockway RA, Nakatani M. Substrate specificity and pH sensitivity of deoxyribonucleotidase and pyrimidine nucleotidase activities in human hemolysates. *Exp Hematol* 1987; 15:1041–47.

Fiske CH, SubbaRow Y. The colorimetric determination of phosphorus. *J Biol Chem* 1925; 66:375–400.

Paglia DE, Valentine WN. Hereditary and acquired defects in the pyrimidine nucleotidase of human erythrocytes. *Current Topics Hematol* 1980; 3:75–109.

(List continued on next page.)

*Primary Examiner*—Louise N. Leary
*Attorney, Agent, or Firm*—Oppenheimer Wolff & Donnelly

[57] ABSTRACT

The present invention provides a highly effective method for determining very low concentrations of heavy metals such as lead, cadminum, mercury, and copper in body fluids. Ratios of d-5'-N/Pyr-5'-N activities which display greater deviation and stronger correlation with blood heavy metal concentrations than absolute Pyr-5'-N activities alone, are utilized to provide a highly sensitive, internally controlled biomarker of low-level lead overburden, for example.

9 Claims, 6 Drawing Sheets

OTHER PUBLICATIONS

Paglia DE, Valentine WN, Dahlgren JG. Effects of low–level lead exposure on pyrimidine 5'-nucleotidase and other erythrocyte enzymes. Possible role of pyrimidine 5'-nucleotidase in the pathogenesis of lead–induced anemia. *J Clin Invest* 1975; 56:1164–69.

Paglia DE, Valentine WN, Fink K. Lead poisoning. Further observations on erythrocyte pyrimidine–nucleotidase deficiency and intracellular accumulation of pyrimidine nucleotides. *J Clin Invest* 1977; 60:1362–66.

Valentine WN, Paglia DE, Fink K, Madokoro G. Lead poisoning: Association with hemolytic anemia, basophilic stippling, erythrocyte pyrimidine 5'-nucleotidase deficiency and intraerythrocytic accumlulation of pyrimidines. *J Clin Invest* 1976; 58:926–32.

Buc HA, Kaplan JC. Red–cell pyrimidine 5'-nucleotidase and lead poisoning. *Clin Chim Acta* 1978; 87:49–55.

Angle CR, McIntire MS. Low level lead and inhibition of erythrocyte pyrimidine nucleotidase. *Environ Res* 1978; 17:296–302.

Brunet M, Vives–Corrons JL, Torra M, Rodamilans M, Pujades A, Corbella J, Pascual A. Assessment of erythrocyte pyrimidine 5'-nucleotidase activity in the detection and early diagnosis of lead poisoning. A comparison with zinc–protoporphyrin. *Medicina Clin* 1988; 91:521–24.

Mohammed–Brahim B, Buchet JP, Lauwerys R. Erythrocyte pyrimidine 5'-nucleotidase activity in workers exposed to lead, mercury or cadmium. *Int Arch Occup Environ Health* 1985; 55:247–255.

Ichiba M, Tomokuni K. Studies on erythrocyte pyrimidine 5'-nucleotidase (P5N) test and its evaluation in workers occupationally exposed to lead. *Int Arch Occup Environ Health* 1990; 62:305–10.

Cook L, Kubitschek C, Stohs S, Angle C. Erythrocyte pyrimidine 5'-nucleotidase and deoxynucleotidase isozymes: metallosensitivity and kinetics. *Drug Chem Toxicol* 1988; 11:195–213.

Ichiba M, Tomokuni K, Sugimoto K. Erythrocyte pyrimidine 5'-nucleotidase test for occupational lead exposure. *Industr Health* 1987; 25:195–213.

Fell GS. Lead toxicity: problems of definition and laboratory evaluation. *Ann Clin Biochem* 1984; 21:453–60.

Mitchell DG, Aldous KM, Ryan FJ. Mass screening for lead poisoning: capillary blood sampling and automated Delves–cup atomic–absorption analysis. *N Y State J Med* 1974; 74:1599–1603.

Piomelli S, Graziano J. Laboratory diagnosis of lead poisoning. *Ped Clinics NA* 1980; 27:843–53.

Wang ST, Pizzolato S, Peter F. Microsampling technique and determination of blood lead by Zeeman atomic absorption spectrophotometry. *Sci Total Environ* 1988; 71:37–43.

Jacobson B, Lockitch G, Quigley G. Improved sample preparation for accurate determination of low concentrations of lead in whole blood by graphite furnace analysis. *Clin Chem* 1991,.37:515–19.

McElvaine MD, Orbach HG, Binder S, Blanksma LA, Maes EF, Krieg RM. Evaluation of the erythrocyte protoporphyrin test as a screen for elevated blood lead levels. *J Pediatr* 1991; 119:548–50.

Hemberg S, Nikkanen J, Mellen G, Lilius H. δ–aminolevulinic acid dehydrase as a measure of lead exposure. *Arch Envrion Health* 1970; 21:140–45.

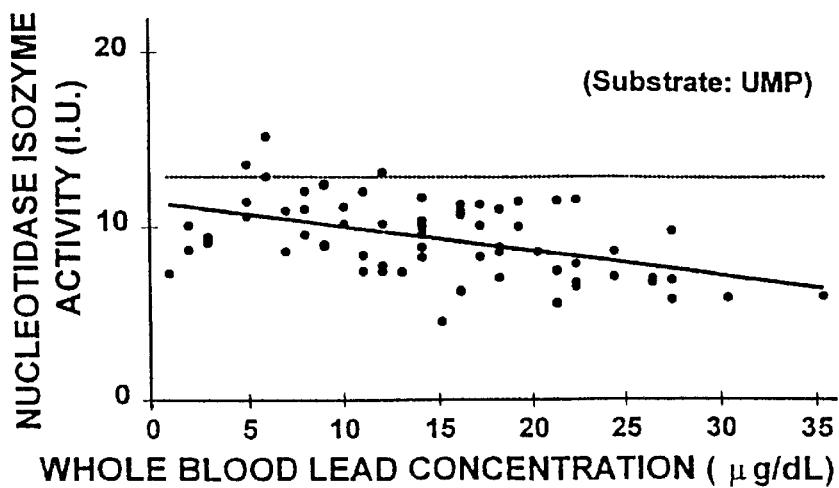
_FIG. 3A._
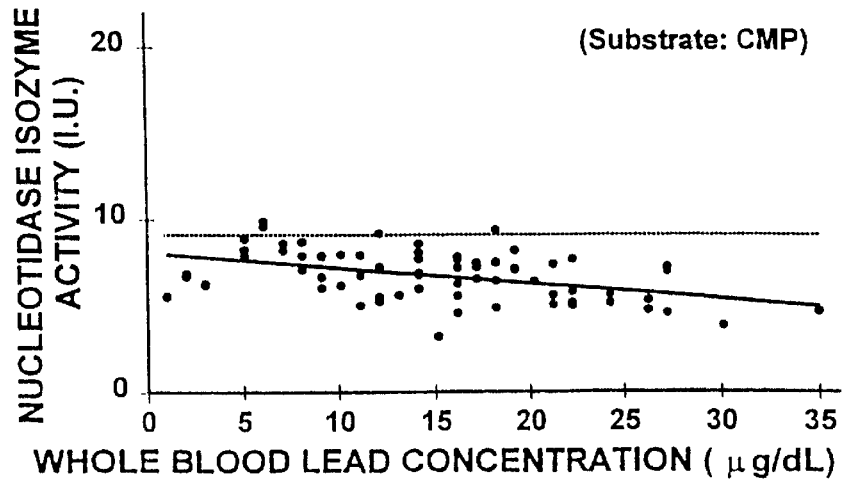
_FIG. 3B._
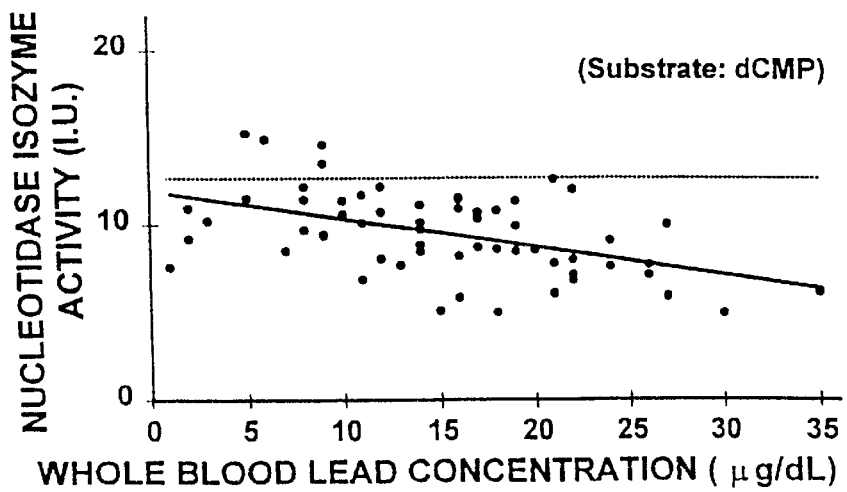
_FIG. 3C._

5,871,947

METHOD FOR THE DETERMINATION OF LOW CONCENTRATIONS OF HEAVY METALS

GOVERNMENT RIGHTS

This invention was made with U.S. Government support. Accordingly, the U.S. Government has certain rights in this invention.

This application claims the benefit of U.S. Provisional application Ser. No. 60/016,596, filed May 8, 1996.

FIELD OF THE INVENTION

This invention relates to the determination of heavy metals in various fluids. In one of its more particular aspects, this invention relates to the measurement of heavy metal concentration in body fluids. In another more particular aspect, the present invention relates to the utilization of nucleotidases as biomarkers of heavy metal overburden in blood.

BACKGROUND OF THE INVENTION

Recent investigations of children have detected adverse effects of exposure to lead at levels previously thought to be innocuous. Irreversible neuropsychological effects have been reported with blood lead levels as low as 10 µg/dL, and several million asymptomatic children are known to have as much as twice that concentration. The most recent revision of standards by the U. S. Public Health Service Centers for Disease Control lowered the recommended intervention level from 25 µg/dL to 10 µg/dL, a concentration at the lower extreme for accurate monitoring by currently practical laboratory techniques. Consequently, a need has emerged for more sensitive and reliable biomarkers of very low body burdens of lead.

SUMMARY OF THE INVENTION

Nucleotidases are membrane-bound or cytosolic enzymes commonly found among animals, plants and microorganisms. They catalyze hydrolytic dephosphorylation of various 5'-ribo- and deoxyribonucleotide substrates to their corresponding nucleosides and inorganic phosphate. For example:

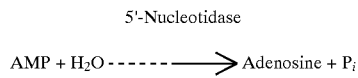

5'-Nucleotidase $$AMP + H_2O \dashrightarrow Adenosine + P_i$$

5'-Nucleotidase (5'-ribonucleotide phosphohydrolase, EC 3.1.3.5) occurs in the form of isozymes. Erythrocyte pyrimidine 5'-nucleotidase (Pyr-5'-N) is highly sensitive in vitro and in vivo to inhibition by heavy metals, whereas its companion isozyme, deoxyribonucleotidase (d-5'-N) is strongly resistant. Pyr-5'-N activity is known to be inversely proportional to whole blood lead concentrations above 40 µg/dL and this relationship is believed to extend into the lowest range of blood lead concentrations now considered to be toxic (<10–20 µg/dL), allowing Pyr-5'-N measurements to serve as highly sensitive biomarkers of minimal lead exposure. Erythrocyte d-5'-N activity, on the other hand, is known to be uniformly normal or elevated, commensurate with reticulocytosis. There is no apparent minimum threshold for Pyr-5'-N inhibition by lead.

The present invention provides a highly effective method for determining very low concentrations of heavy metals such as lead, cadminum, mercury, and copper in body fluids. Ratios of d-5'-N/Pyr-5'-N activities which display greater deviation and stronger correlation with blood heavy metal concentrations than absolute Pyr-5'-N activities alone, are utilized to provide a highly sensitive, internally controlled biomarker of low-level lead overburden, for example.

The method of the present invention is useful for determining low concentrations of heavy metals, such as lead, in fluids which contain both Pyr-5'-N and its isozyme d-5'-N, such as human body fluids. The method consists of measuring the ratio of the activity of d-5'-N to the activity of Pyr-5'-N in a sample fluid and selecting the concentration of heavy metal corresponding to the measured ratio. Correspondence between heavy metal concentrations and activity ratios can be established, for example, from plots of activity ratios against heavy metal concentrations or from tabulated data relating such ratios and concentrations.

BRIEF DESCRIPTION OF THE DRAWINGS

FIG. 3(a) is a plot of Pyr-5'-N activity of UMP substrate for whole blood lead concentrations ranging from about 1 µg/dL to 35 µg/dL.

FIG. 3(b) is a similar plot of Pyr-5'-N activity on CMP.

FIG. 3(c) is a similar plot of Pyr-5'-N activity on dCMP.

DESCRIPTION OF THE PREFERRED EMBODIMENTS

Figure 1A:
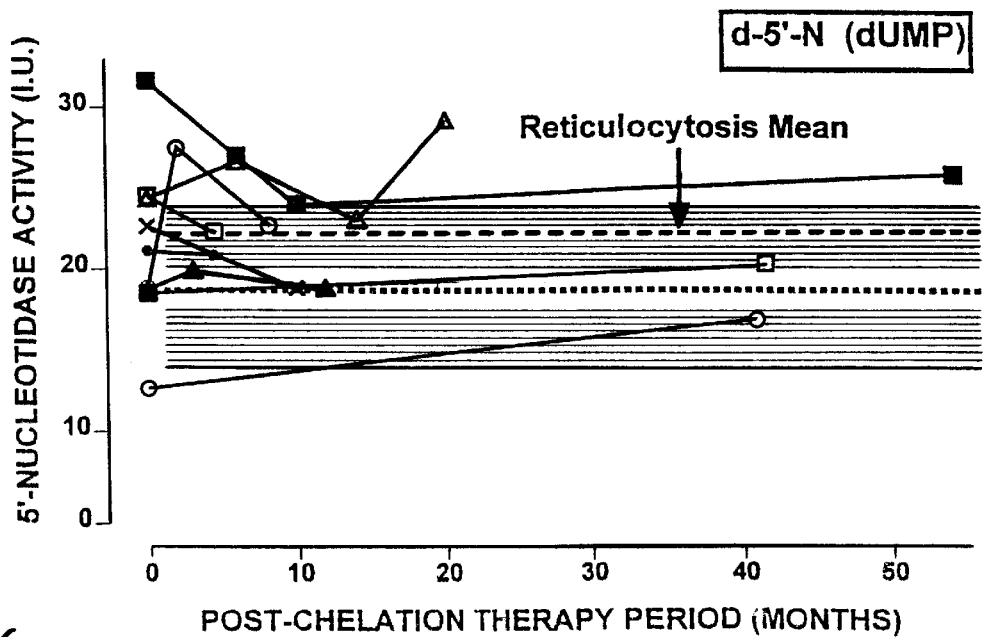
FIG. 1(a) is a graph of a d-5'--N activity on dUMP substrate plotted over a period of about 50 months in a discrete number of human blood samples.

The presence of Pyr-5'-N in human erythrocytes was first revealed by studies among kindred afflicted with a hemolytic syndrome induced by hereditary deficiency Unlike other nucleotidases, the red cell isozyme displayed an unusual substrate specificity restricted to UMP, CMP and dCMP.

Subsequent studies of Pyr-5'-N-deficient erythrocytes revealed the existence of a second nucleotidase isozyme, d-5'-N, which was optimally active at acidic pH with a variety of both purine and pyrimidine deoxyribonucleotide substrates (dIMP>>dUMP>dGMP>dTMP=dAMP>>dCMP). These biochemical characteristics are presumed to represent evolutionary adaptations to allow clearance of RNA and DNA degradation products during erythroblast and reticulocyte maturation, while simultaneously preventing loss of adenine nucleotides (AMP, ADP, and ATP) that are crucial to normal metabolism, function and survival of mature erythrocytes. The hallmarks of severe hereditary deficiency of Pyr-5'-N include enormous intracellular accumulations of pyrimidine compounds, normally not detectable in mature erythrocytes, and prominent basophilic stippling of circulating red cells, a morphologic reflection of undergraded or partially degraded ribonucleoprotein.

Studies to define the biochemical characteristics of these two previously unknown erythrocyte enzymes indicated that Pyr-5'-N was extraordinarily sensitive to heavy metal inactivation in vitro, whereas the d-5'-N isozyme was at least 100-fold more resistant under comparable conditions. Micromolar amounts of lead, cadmium, mercury, and copper distinctly inhibited Pyr-5'-N, with 50% inactivation occurring between 1 $\mu$M and 10 $\mu$M divalent lead concentrations. This sensitivity to lead inhibition, and the occurrence of prominent basophilic stippling in both hereditary deficiency hemolytic anemia and in severe plumbism, suggested a possible causal relationship between lead-induced inactivation of Pyr-5'-N and the hemolytic component of the consequent anemia. This was eventually confirmed by studies of subjects with acute and chronic industrial lead exposures in whom Pyr-5'-N activity was found to be inversely proportional to blood lead concentration. When blood lead levels reached about 200 $\mu$g/dL, Pyr-5'-N was suppressed to 5–15% of normal control means, the same range usually seen in severe hereditary deficiency states. At that level of Pyr-5'-N activity, in both hereditary and acquired deficiencies, affected red cells begin to accumulate abnormal pyrimidine compounds, basophilic stippling appears, and the anemia of lead overburden acquires a hemolytic component in addition to the multifactorial effects on hemoglobin synthesis, membrane integrity, and the like.

Measurements of Pyr-5'-N have now become broadly accepted as a reliable indicator of moderate or severe lead toxicity, but there are few data relative to their value in the lowest range of lead exposure that has recently become the focus of major clinical concern. In this region of minimal overburden, all of the conventional laboratory parameters used to assess lead intoxication become progressively less sensitive and less dependable. Quantitative blood lead assays have been the method of choice for screening purposes, but these must be performed by specialized laboratories, and they are subject to error from environmental contamination and analytical variation. Standard assays for blood lead are also inadequate in accuracy and precision to discriminate clinically significant elevations from baseline at the 10 $\mu$g/dL threshold, many laboratories simply reporting extremely low values as "less than 5 $\mu$g/dL". Additionally, because of the complex equilibria involved, quantitative assays of blood lead principally reflect recent exposures and are poorly reliable as a gauge of total body burdens.

Other biomarkers currently available for detecting or monitoring minimal body burdens of lead also have major limitations. Erythrocyte protoporphyrin is not sufficiently sensitive to identify children with blood lead levels below about 25 $\mu$g/dL, and therefore it is no longer a recommended screening test for lead intoxication. Urinary concentrations of δ-aminolevulinic acid are useful, but standardized methods for such assays have been difficult to implement. Determinations of erythrocyte δ-aminolevulinic acid dehydratase are adversely affected by the inherent instability of this enzyme.

These limitations in methodology, coupled with progressively increasing clinical concerns about the deleterious effects of even trace quantities of lead and other heavy metals, prompted a reevaluation of erythrocyte Pyr-5'-N as a potential biomarker of minimal body burdens. Data were obtained from 10 children with moderate lead intoxication (initial blood lead=55–92 $\mu$g/dL), followed as long as 54 months during and after chelation therapy. Nucleotidase assays with multiple substrates at acidic and alkaline pH optimal for discrimination between the two major isozymes were performed. Activities for d-5'-N were found to be generally normal or slightly elevated in all subjects. By contrast, Pyr-5'-N activities in the same individuals were moderately or markedly decreased at each corresponding time. Significant depressions in Pyr-5'-N activity persisted despite reductions in some blood lead concentrations to as low as 9–25 $\mu$g/dL.

In another group 17 children reviewed retrospectively, routine screening assays revealed blood lead concentrations of <5–18 $\mu$g/dL, and most exhibited Pyr-5'-N activities slightly to moderately below control means, again with entirely normal d-5'-N activities. This group was prospectively expanded to 71 children with blood lead levels of 1–35 $\mu$g/dL, and nucleotidase activities were assayed with multiple substrates at appropriate pH optima. Results of these studies indicated that the inverse correlation between Pyr-5'-N activity and blood lead concentration, previously well established for levels of toxicity above 35–40 $\mu$g/dL, appears to extend linearly throughout the entire lower range of measurable overburdens with no evidence of a threshold effect.

While these data support the value of Pyr-5'-N as a biomarker for very low levels of lead intoxication, there are inherent limitations in the use of quantitative Pyr-5'-N activity alone as a direct correlate of the magnitude of lead overburden. Because circulating erythrocytes are incapable of protein synthesis, their enzymes' catalytic activities decline at variable but characteristic rates once they mature beyond the reticulocyte stage. Pyr-5'-N is one of several enzymes that exhibits significantly higher activities in reticulocytes and young erythrocytes, so decrements in absolute Pyr-5'-N activity induced by lead can be easily masked by a slight reticulocytosis or shift to a younger mean cell age, which often occurs in the anemia of lead toxicity itself Fortunately, the activity of its companion isozyme, d-5'-N, is similarly dependent on red cell age. Since d-5'-N is strongly resistant to heavy-metal inhibition, the ratio of these two activities minimizes or cancels any artifact due to reticulocytosis or changes in mean cell age, providing a more accurate reflection of the true inhibitory effect of lead on the Pyr-5'-N isozyme.

The following examples illustrate various aspects of the present invention.

EXAMPLE 1

Leukocyte- and platelet-free suspensions of erythrocytes were prepared by filtration of whole blood through columns packed with equal parts α-cellulose and microcrystalline cellulose (Sigmacell-50, Sigma Chemical Co., St. Louis, Mo.) in isotonic saline, followed by three washes and resuspension in isotonic saline at 4° C. to final counts of approximately 3×10 $\mu$L. Aliquots were lysed by sonication and dialyzed overnight at 4° C. against 200 vol 0.154M NaCl containing 10 mM Tris hydrochloride buffer, pH 8.0, 10 mM $MgCl_2$, 0.02 mM EDTA, and 1 mM 2-mercaptoethanol to remove endogenous phosphates from the hemolysates. A second 2-h dialysis against fresh solution was performed just prior to nucleotidase assays. Hemoglobin concentrations in the final preparations ranged from 10 to 12 g/dL as determined by ultraviolet absorption following conversion to cyanmethemoglobin.

Aliquots of dialyzed hemolysates were incubated at 37° C. for 2 h with either 0.05 M Tris-HCl buffer, pH 7.4, (for Pyr-5'-N) or 0.3M Tris-maleate buffer, pH 6.0, (for d-5'-N) containing final concentrations of 8.5 mM $MgCl_2$, 0.5 mM dithiothreitol, and 2.3 mM nucleotide monophosphate. All nucleotide substrates were obtained from Sigma Chemical Co., St. Louis, Mo., and included cytidine, uridine, and guanosine 5'-monophosphates (CMP, UMP, GMP) as disodium salts; adenosine, deoxyadenosine, deoxyinosine, deoxyuridine, deoxythymidine, and xanthosine 5'monophosphates (AMP, dAMP, dIMP, dUMP, dTMP, XMP) as monosodium salts, and inosine, deoxycytidine and deoxyguanosine 5'-monophosphates (IMP, dCMP, dGMP) as free acids. At the end of each 2-h incubation, reactions were terminated by deproteinization with equal volumes of 1.2N perchloric acid. Individual substrates were added to reagent blanks after perchloric deproteinization. Concentrations of inorganic phosphate ($P_i$) generated by nucleotidase activity were then determined by the Fiske and SubbaRow method. Units of nucleotidase activity were defined as micromoles of inorganic phosphate generated per hour per gram of hemoglobin. Statistical analyses of nucleotidase data were performed with STATISTICA for Windows, Version 4.5, StatSoft, Inc., Tulsa, Okla., 1993.

Figure 1B:
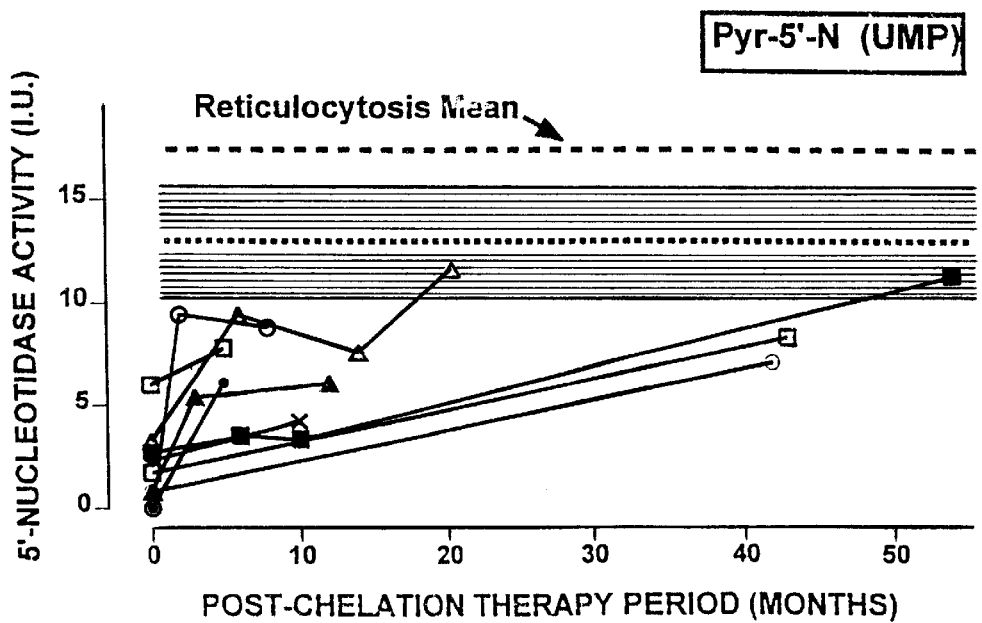
FIG. 1(b) is a similar graph of Pyr-5'-N activity on UMP.

FIG. 1 presents data from ten children with initial blood lead levels of 55–92 μg/dL (mean 74 μg/dL) who received chelation therapy and were followed over periods of 5 to 54 months subsequently. Average erythrocyte protoporphyrin concentration in this group before chelation was 669 μg/dL packed red cells (pRBC) with a range of 141–1,725 μg/dL pRBC (reference interval=<35 μg/dL pRBC). In duplicate assays with the two principal substrates for Pyr-5'-N, UMP and CMP (latter not shown), nine of the ten subjects initially displayed Pyr-5'-N activities more than 3 SD below the laboratory mean for nonsegregated normal controls, and the tenth was more than 2 SD below that mean. Simultaneous assays of d-5'-N with dUMP and dIMP as substrates (latter not shown) yielded normal or above values throughout the entire study period, indicating the absence of significant in vivo inhibition of the d-5'-N isozyme throughout that range of moderate lead overburden.

Effectiveness of chelation therapy was indicated in multiple follow-up specimens by rapid declines in blood lead and erythrocyte protoporphyrin concentrations. As shown in FIG. 1, Pyr-5'-N activities exhibited a general tendency to increase rapidly as lead was cleared from the peripheral blood, but the rates of change soon became asymptotic, and eight of ten patients remained more than I SD below normal control mean for the population at large, despite decreasing blood lead values to as low as 9–29 μg/dL. Simultaneous assays of red cell d-5'-N continued to show normal (or greater) activities in all ten subjects.

It should be noted that the presence of reticulocytes or a shift to a younger mean cell age in peripheral blood specimens results in increased activities of many erythrocyte enzymes, Pyr-5'-N and d-5'-N being among those showing the greatest elevations. As indicated by "Reticulocytosis Mean" in FIG. 1, average Pyr-5'-N (UMP) activity for 15 subjects with a mean reticulocytosis of 8.7% (range= 5.2–18.7%) was 4 units higher than the population at large. Comparable elevations in d-5'-N activity occur with reticulocytosis. In FIG. 1, d-5'-N activities were frequently elevated well above normal controls, commensurate with reticulocyte counts of 3–4% that were common among these subjects, so the observed depressions in absolute Pyr-5'-N activities were accordingly even more significant.

EXAMPLE 2

Figure 2:
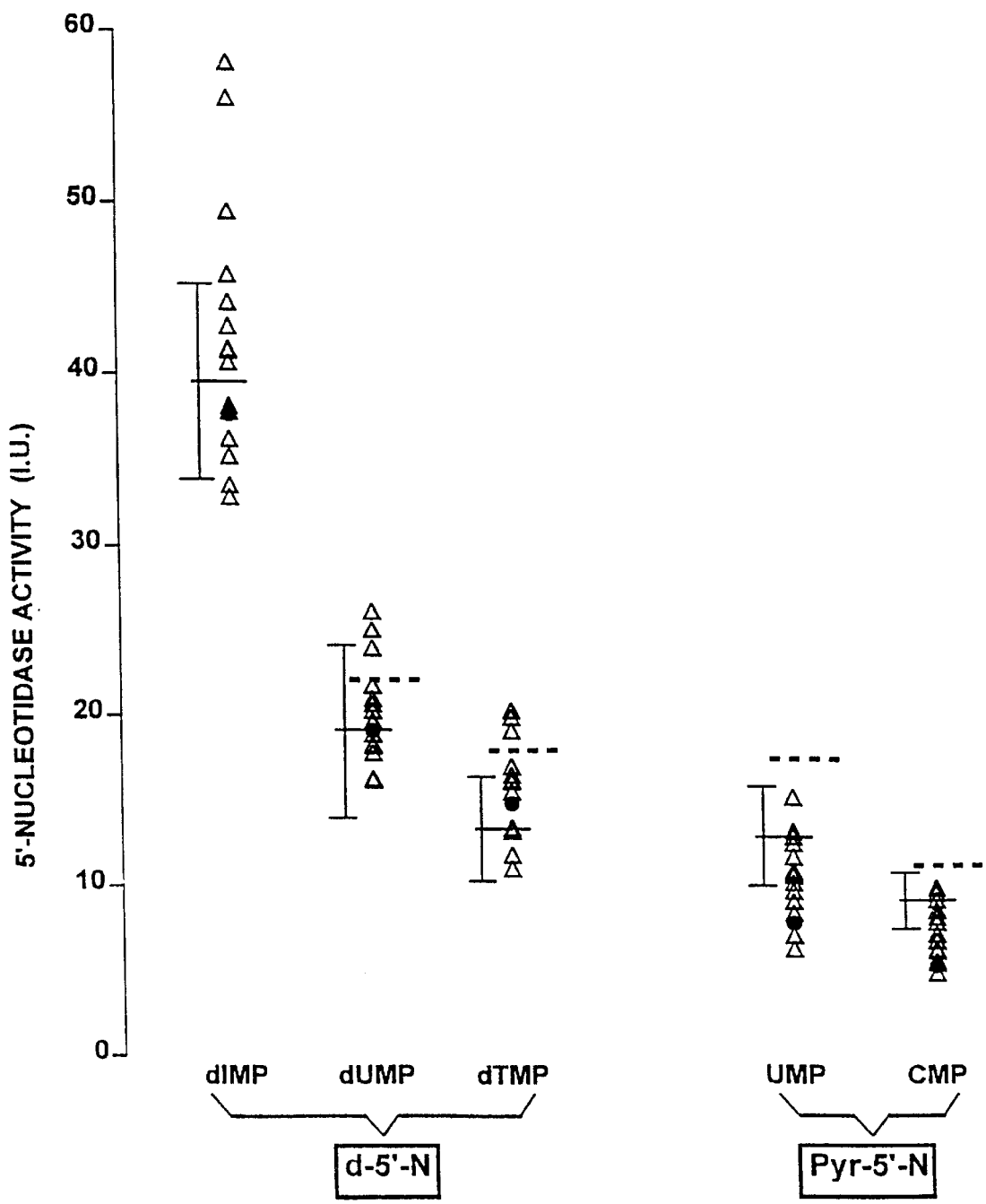
FIG. 2 is a plot of instantaneous activities of d-5'-N and Pyr-5'-N on various substrates in a discrete number of human blood samples.

Retrospective review of data from another group of 17 children provided additional support for the potential value of Pyr-5'-N measurements in detection of minimal lead exposures. Routine screening assays had revealed whole blood lead levels of <5–18 μg/dL (mean=1 1.5 μg/dL). FIG. 2 compares d-5'-N activities measured with three different substrates relative to Pyr-5'-N assayed with its two principal substrates, UMP and CMP. A consistent tendency for Pyr-5'-N activities to fall below normal mean values contrasts with the normal or slight elevation of d-5'-N activities in these same subjects. One child, designated with a solid symbol in FIG. 2, had an uncertain history of possible lead exposure 1–2 years previously. Her blood lead and erythrocyte protoporphyrin concentrations were 12 and 63 μg/dL, respectively. As with the children shown in FIG. 1 the marked depression in her Pyr-5'-N activities strongly suggests that these measurements alone may not adequately reflect total body burdens of lead or its biological consequences.

EXAMPLE 3

Data in FIG. 3 demonstrate the tendency for Pyr-5'-N activity to diminish as a function of blood lead concentration in 71 subjects with no known history of lead exposure in whom screening tests revealed lead values in the range of 1 to 35 μg/dL whole blood. This interdependence between Pyr-5'-N and blood lead concentration was apparent regardless of which nucleotide served as substrate, UMP, CMP or dCMP.

EXAMPLE 4

Figure 4A:
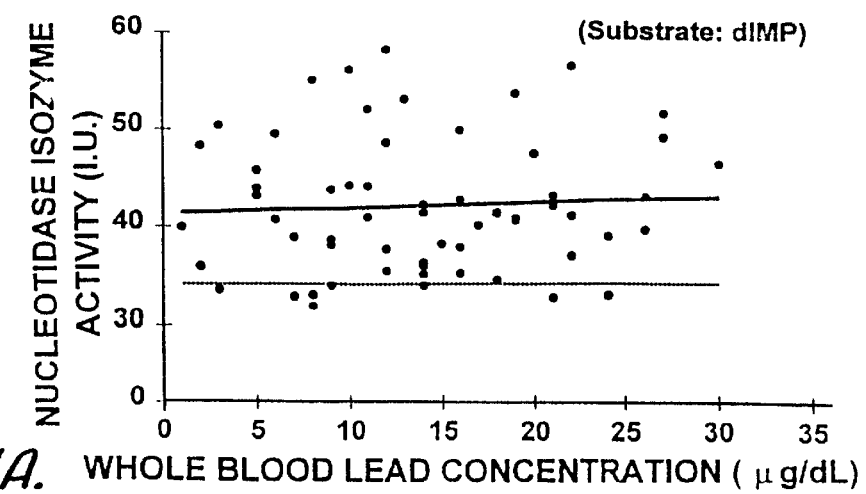
FIG. 4(a) is a plot of d-5'-N activity on dIMP substrate for whole blood lead concentrations ranging from about 1 µg/dL to 35 µg/dL.
Figure 4B:
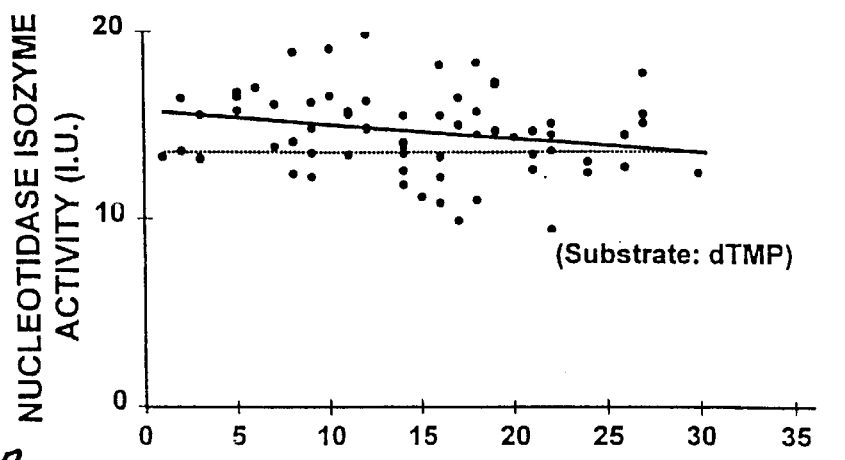
FIG. 4(b) is a similar plot of d-5'-N activity on dTMP.
Figure 4C:
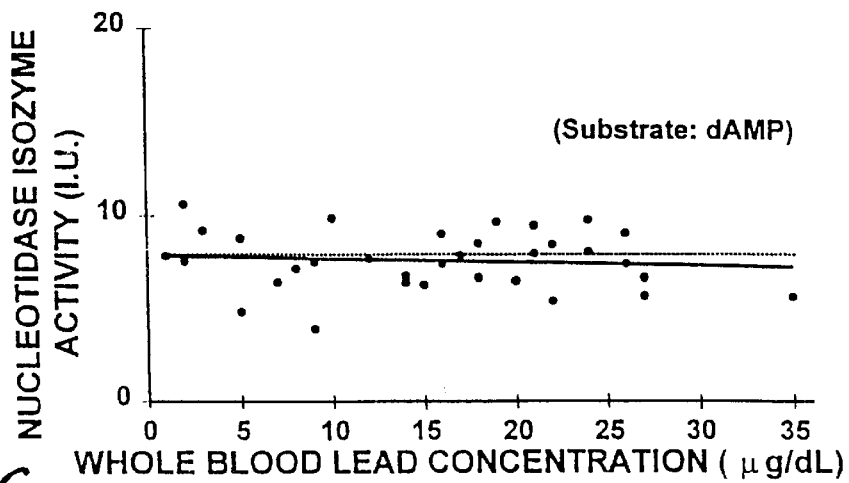
FIG. 4(c) is a similar plot of d-5'-N activity on dAMP.

Data in FIG. 4 indicate that d-5'-N activity, measured with three specific substrates (dIMP, dTMP and dAMP), showed no consistent correlation with blood lead concentration over this same range, substantiating this isozyme's known resistance to heavy-metal inactivation in vitro.

In FIGS. 3 and 4, most of the activities of both Pyr-5'-N and d-5'-N fell within the reference interval previously established for these assays in normal control subjects unselected for age, gender or ethnicity, demonstrating that overburdens in this lower range of blood lead concentrations cannot be reliably detected by depression of absolute Pyr-5'-N activity alone.

The following example illustrates the use of ratios of enzyme activities rather than the activity of either Pyr-5'-N or d-5'-N alone.

EXAMPLE 5

Figure 5A:
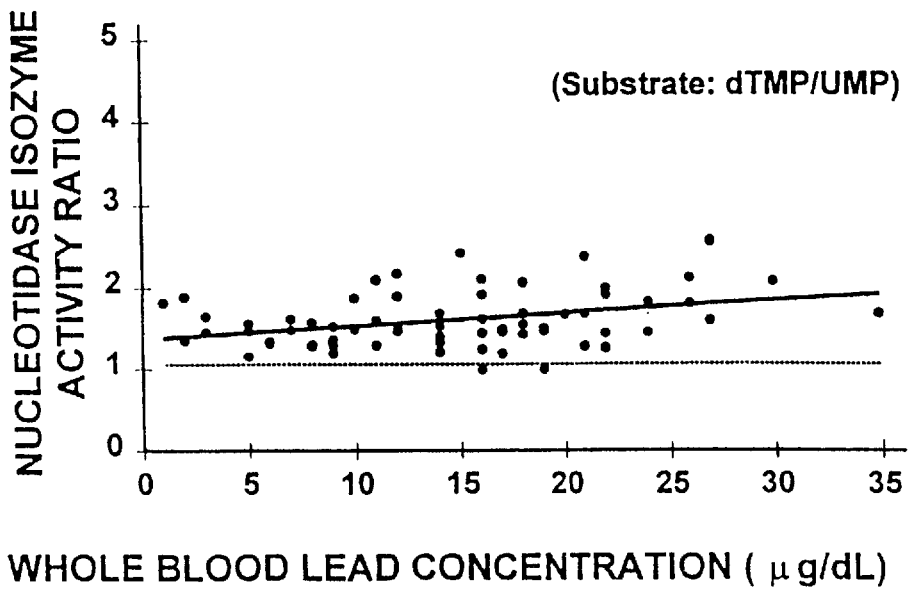
FIG. 5(a) is a plot of ratios of d-5'-N activity on dTMP substrate to Pyr-5'-N activity on UMP substrate for whole blood lead concentrations ranging from about 1 µg/dL to 35 µg/dL.
Figure 5B:
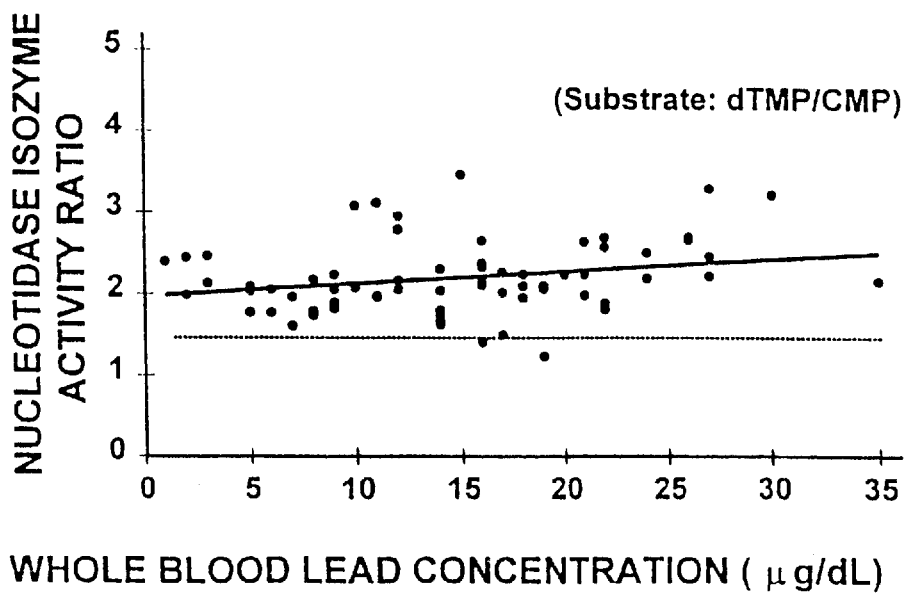
FIG. 5(b) is a similar plot of ratios of d-5'-N activity on dTMP substrate to Pyr-5'-N activity on CMP substrate.
Figure 6:
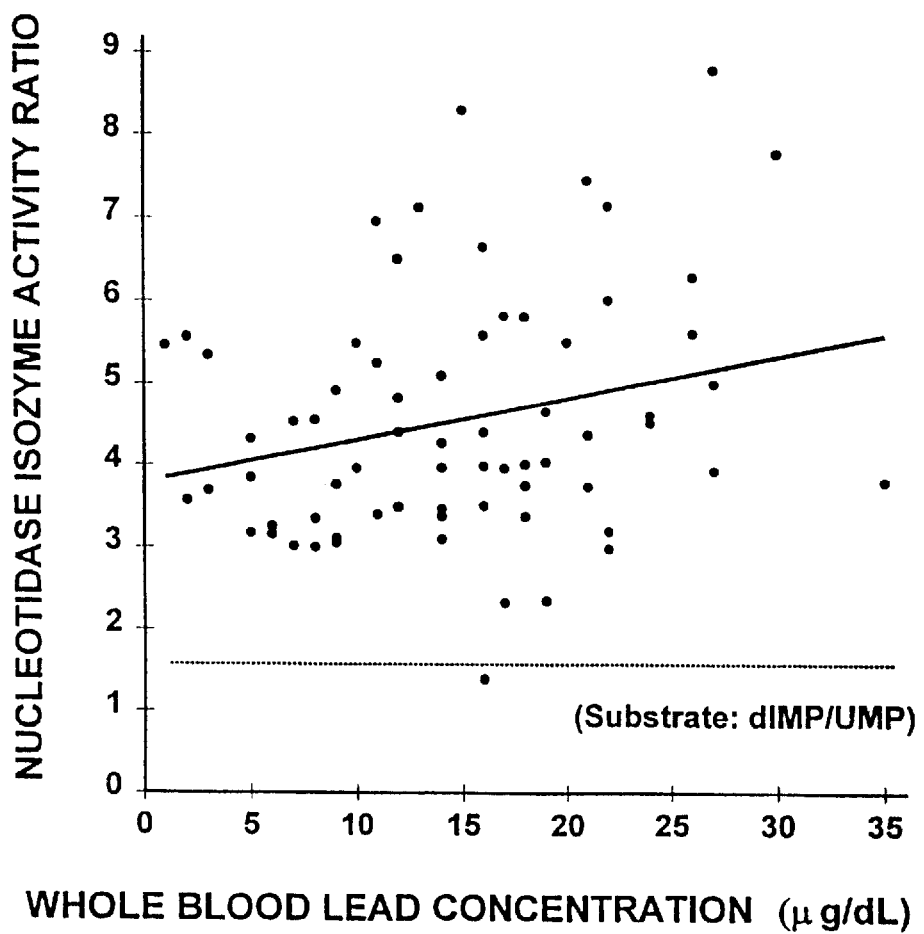
FIG. 6 is a plot of ratios of d-5'-N activity on dIMP substrate to Pyr-5'-N activity on UMP substrate for whole blood lead concentrations ranging from about 1 µg/dL to 35 µg/dL.

As shown in FIGS. 5 and 6, ratios of the isozyme activities of d-5'-N to Pyr-5'-N with various substrates were almost invariably well above ratio values for normal controls. Quantitatively, the greatest deviation in d-5'-N/Pyr-5'-N activity ratios occurred when dIMP and UMP were used as substrates as shown in FIG. 6.

Thus, tandem measurements of d-5'-N and Pyr-5'-N activities provide a more reliable and sensitive biological indicator of overburdens corresponding to blood lead levels below 10–20 of μg/dL, than measurements of d-5'-N or Pyr-5'-N activities alone.

Although the present invention has been described with reference to preferred embodiments, workers skilled in the art will recognize that changes may be made in form and detail without departing from the spirit and scope of the invention.

REFERENCES

1. U.S. Public Health Service. Preventing lead poisoning in young children: A statement by the Centers for Disease Control. Atlanta: CDC, 1984.
2. Bellinger D, Leviton A, Watemaux C, Needleman H, Rabinowitz M. Longitudinal analyses of prenatal and postnatal lead exposure and early cognitive development. *N Engl J Med* 1987; 316:1037–43.
3. Agency for Toxic Substances and Disease Registry. The nature and extent of lead poisoning in children in the United States: A report to Congress. *Atlanta:ATSDR*, 1988.
4. Valentine W N, Fink K, Paglia D E, Harris S R, Adains W S. Hereditary hemolytic anemia with human erythrocyte pyrimidine 5'-nucleotidase deficiency. *J Clin Invest* 1974; 54:866–79.
5. Paglia D E, Valentine W N. Characteristics of a pyrimidine-specific 5'-nucleotidase in human erythrocytes. *J Biol Chem* 1975; 7973–79.
6. Paglia D E, Valentine W N, Keitt A S, Brockway R A, Nakatani M. Pyrimidine nucleotidase deficiency with active dephosphorylation of dTNT: Evidence for existence of thymidine nucleotidase in human erythrocytes. *Blood* 1983;62: 1147–49.
7. Paglia D E, Valentine W N, Brockway R A. Identification of thymidine nucleotidase and deoxyribonucleotidase activities among normal isozymes of 5'-nucleotidase in human erythrocytes. *Proc Natl Acad Sci* (U.S.A.) 1984; 81:588–92.
8. Paglia D E, Valentine W N, Brockway R A, Nakatani M. Substrate specificity and pH sensitivity of deoxyribonucleotidase and pyrimidine nucleotidase activities in human hemolysates. *Exp Hematol* 1987; 15:1041–47.
9. Fiske C H, SubbaRow Y. The colorimetric determination of phosphorus. *J Biol Chem* 1925; 66:375–400.
10. Paglia D E, Valentine W N. Hereditary and acquired defects in the pyrimidine nucleotidase of human erythrocytes. *Current Topics Hematol* 1980, 3:75–109.
11. Paglia D E, Valentine W N, Dahlgren J G. Effects of low-level lead exposure on pyrimidine 5'-nucleotidase and other erythrocyte enzymes. Possible role of pyrimidine 5'-nucleotidase in the pathogenesis of lead-induced anemia. *J Clin Invest* 1975; 56:1164–69.
12. Paglia D E, Valentine W N, Fink K. Lead poisoning. Further observations on erythrocyte pyrimidine-nucleotidase deficiency and intracellular accumulation of pyrimidine nucleotides. *J Clin Invest* 1977; 60:1362–66.
13. Valentine W N, Paglia D E, Fink K, Madokoro G. Lead poisoning: Association with hemolytic anemia, basophilic stippling, erythrocyte pyrimidine 5'-nucleotidase deficiency and intraerythrocytic accumlulation of pyrimidines. *J Clin Invest* 1976; 58:926–32.
14. Buc H-A, Kaplan J-C. Red-cell pyrimidine 5'-nucleotidase and lead poisoning. *Clin Chim Acta* 1978; 87:49–55.
15. Angle C R, McIntire M S. Low level lead and inhibition of erythrocyte pyrimidine nucleotidase. *Environ Res* 1978; 17:296–302.
16. Brunet M, Vives-Corrons J L, Torra M, Rodamilans M, Pujades A, Corbella J, Pascual A. Assessment of erythrocyte pyrimidine 5'-nucleotidase activity in the detection and early diagnosis of lead poisoning. A comparison with zinc-protoporphyrin. *Medicina Clin* 1988; 91:521–24.
17. Mohammed-Brahim B, Buchet J P, Lauwerys R. Erythrocyte pyrimidine 5'-nucleotidase activity in workers exposed to lead, mercury or cadmium. *Arch Occup Environ Health* 1985; 55:247–255.
18. Ichiba M, Tomokuni K. Studies on erythrocyte pyrimidine 5'-nucleotidase (P5N) test and its evaluation in workers occupationally exposed to lead. *Int Arch Occup Environ Health* 1990; 62:305–10.
19. Cook L, Kubitschek C, Stohs S, Angle C. Erythrocyte pyrimidine 5'-nucleotidase and deoxynucleotidase isozymes: metallosensitivity and kinetics. *Drug Chem Toxicol* 1988; 11:195–213.
20. Ichiba M, Tomokuni K, Sugimoto K. Erythrocyte pyrimidine 5'-nucleotidase test for occupational lead exposure. *Industr Health* 1987; 25: 195–213.
21. Fell G S. Lead toxicity: problems of definition and laboratory evaluation. *Ann Clin Biochem* 1984; 21:453–60.
22. Mitchell D G. Aldous K M, Ryan F J. Mass screening for lead poisoning: capillary blood sampling and automated Delves-cup atomic-absorption analysis. *N Y State J Med* 1974; 74:1599–1603.
23. Piomelli S, Graziano J. Laboratory diagnosis of lead poisoning. *Ped Clinics NA* 1980; 27:843–52.
24. Wang S T, Pizzolato S, Peter F. Microsampling technique and determination of blood lead by Zeeman atomic absorption spectrophotomery. *Sci Total Environ* 1988; 71:37–43.
25. Jacobson B, Lockitch G, Quigley G. Improved sample preparation for accurate determination of low concentrations of lead in whole blood by graphite furnace analysis. *Clin Chem* 1991, 37:515–19.
26. McElvaine M D, Orbach H G, Binder S, Blanksma L A, Maes E F, Krieg R M. Evaluation of the erythrocyte protoporphyrin test as a screen for elevated blood lead levels. *J Pediatr* 1991; 119:548–50.
27. Hemberg S, Nikkanen J, Mellen G, Lilius H. δ-aminolevulinic acid dehydrase as a measure of lead exposure. *Arch Environ Health* 1970; 21:140–45.

What is claimed is:

1. A method for determining the concentration of a heavy metal in a fluid containing both erythrocyte pyrimidine 5'-nucleotidase (Pyr-5'-N) and its isozyme deoxyribonucleotidase (d-5'-N) comprising measuring the ratio of the d-5'-N activity to the Pyr-5'-N activity and selecting the heavy metal concentration corresponding to the measured ratio.

2. The method of claim 1 wherein said heavy metal is a member selected from the group consisting of lead, cadmium, mercury, and copper.

3. The method of claim 1, wherein the fluid being tested is a human body fluid.

4. The method of claim 3, wherein said human body fluid is whole blood.

5. The method of claim 1, wherein said d-5'-N activity is measured on a substrate selected from the group consisting of deoxyinosine 5'-monophosphate (dIMP), deoxyuridine 5'-monophosphate (dUMP), deoxyguanosine 5'-monophosphate (dGMP), deoxythyinidine 5'-monophosphate (dTMP), deoxyadenosine 5'-monophosphate (dAMP), and deoxycytidine 5'-monophosphate (dCMP).

6. The method of claim 1, wherein said Pyr-5'-N activity is measured on a substrate selected from the group consisting of uridine 5'-monophosphate (UMP), cytidine 5'-monophosphate (CMP), and deoxycytidine 5'-monophosphate.

7. The method of claim 1, wherein the heavy metal concentration is a lead concentration within the range of <10 μg/dL to 20 μg/dL.

8. A method for determining the concentration of a heavy metal in a fluid, which fluid contains both erythrocyte pyrimidine 5'-nucleotidase (Pyr-5'-N) and its isozyme deoxyribonucleotidase (d-5'-N) comprising measuring the ratio of the activity of d-5'-N to the activity of Pyr-5'-N in said fluid, comparing the measured ratio with a plot of ratios of the activities of d-5'-N to the activities of Pyr-5'-N against heavy metal concentrations corresponding to said ratios, and selecting the heavy metal concentration corresponding to said measured ratio.

9. A method for determining the concentration of a heavy metal in a fluid, which fluid contains both erythrocyte pyrimidine 5'-nucleotidase (Pyr-5'-N) and its isozyme deoxyribonucleotidase (d-5'-N) comprising measuring the ratio of the activity of d-5'-N to the activity of Pyr-5'-N in said fluid, comparing the measured ratio with tabulated values of heavy metal concentrations corresponding to the ratios of activities of d-5'-N to activities of Pyr-5'-N, and selecting the heavy metal concentration corresponding to said measured ratio.

* * * * *